(12) United States Patent
Bennett

(10) Patent No.: US 7,926,390 B2
(45) Date of Patent: Apr. 19, 2011

(54) COUPLING DEVICE WITH CONFIGURABLE ACTUATOR

(75) Inventor: Jeffrey Bennett, Pottstown, PA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 11/384,189

(22) Filed: Mar. 16, 2006

(65) Prior Publication Data

US 2006/0248988 A1 Nov. 9, 2006

Related U.S. Application Data

(63) Continuation-in-part of application No. 11/244,301, filed on Oct. 5, 2005, now abandoned.

(60) Provisional application No. 60/678,245, filed on May 5, 2005.

(51) Int. Cl.
*B25B 13/46* (2006.01)

(52) U.S. Cl. ........... 81/62; 81/63.1; 81/63.2; 81/177.85; 81/438; 81/473

(58) Field of Classification Search .............. 81/62, 63.1, 81/63.2, 177.85, 473, 438; 73/862.23, 862.22, 73/862.21
See application file for complete search history.

(56) References Cited

U.S. PATENT DOCUMENTS

| | | | | |
|---|---|---|---|---|
| 2,300,392 A | * | 11/1942 | Austin | ............................. 173/93 |
| 2,627,330 A | | 2/1953 | Gantz | |
| 2,693,123 A | * | 11/1954 | Fish | ................. 81/58.2 |
| 2,986,248 A | | 5/1961 | Rock | |
| 3,621,739 A | | 11/1971 | Seablom | |
| 3,908,487 A | | 9/1975 | Plaw | |
| 4,448,098 A | * | 5/1984 | Totsu | ................................. 81/467 |
| 4,669,339 A | | 6/1987 | Cartwright | |
| 4,674,368 A | | 6/1987 | Surowiecki | |
| 4,777,852 A | | 10/1988 | Herman et al. | |
| 5,535,648 A | | 7/1996 | Braun et al. | |
| 5,576,501 A | * | 11/1996 | Huang | ........................ 73/862.23 |

(Continued)

FOREIGN PATENT DOCUMENTS

GB 578434 6/1946

(Continued)

*Primary Examiner* — Robert Scruggs
(74) *Attorney, Agent, or Firm* — Michael F. Scalise

(57) ABSTRACT

A driving tool includes a shank, a sleeve, and a return spring disposed therebetween. The shank has a ball recess with a ball received therein. The shank has an interior interface adapted for receiving a tool bit. The ball recess substantially extends into the interior interface. The sleeve mounts on the shank to slide between limits. The sleeve has a first interior ball release recess followed by an interior ball lock surface and then a second interior ball release recess. The release recesses and surface are oriented with respect to the ball recess so as to permit selective displacement of the same over the ball recess to unlock the ball with movement in either direction. A return spring is disposed between the shank and the sleeve. The spring has a first and second end. One of the ends of the spring acts against a feature fixed with the shank and the other end of the spring acts against a feature fixed with the sleeve in a manner so as to permit selective displacement of the ball release recess and lock surface over the ball recess. The position of least spring potential energy is the position with the surface located just above the ball recess so as to tend to lock the ball into engagement with tool bit when the sleeve is in a rest position.

24 Claims, 9 Drawing Sheets

U.S. PATENT DOCUMENTS

| | | | |
|---|---|---|---|
| 5,586,847 A * | 12/1996 | Mattern et al. | 408/239 A |
| 5,613,585 A * | 3/1997 | Tiede | 192/43.1 |
| 5,619,891 A | 4/1997 | Tiede | |
| 5,683,404 A | 11/1997 | Johnson | |
| 5,687,623 A | 11/1997 | Hsieh | |
| 5,687,820 A | 11/1997 | Lin | |
| 5,778,743 A | 7/1998 | Tiede | |
| 5,836,430 A * | 11/1998 | Vasudeva | 192/43.2 |
| 5,873,288 A | 2/1999 | Gauthier et al. | |
| 5,894,766 A * | 4/1999 | Yang | 81/60 |
| 5,943,755 A | 8/1999 | Gauthier et al. | |
| 5,967,277 A | 10/1999 | Walter | |
| 5,996,452 A * | 12/1999 | Chiang | 81/429 |
| 6,073,522 A | 6/2000 | Carnesi | |
| 6,109,140 A | 8/2000 | Roberts et al. | |
| 6,142,277 A * | 11/2000 | Barnett et al. | 192/43.1 |
| 6,206,160 B1 | 3/2001 | Chen | |
| 6,543,959 B1 * | 4/2003 | Jore | 403/322.2 |
| 6,598,499 B1 * | 7/2003 | Ernst | 81/53.2 |
| 6,817,458 B1 * | 11/2004 | Gauthier | 192/43.1 |
| 6,820,522 B2 * | 11/2004 | Hu | 81/176.3 |
| 7,089,829 B2 * | 8/2006 | Chen | 81/63.1 |
| 7,181,997 B1 * | 2/2007 | Rinner et al. | 81/58.4 |
| 2002/0017169 A1 | 2/2002 | Hu | |
| 2003/0110901 A1 | 6/2003 | Shiao | |
| 2004/0026877 A1 * | 2/2004 | Taylor et al. | 279/75 |
| 2004/0056435 A1 * | 3/2004 | Bedi et al. | 279/75 |
| 2005/0076752 A1 * | 4/2005 | Nessbaum et al. | 81/451 |
| 2005/0284270 A1 * | 12/2005 | Huang | 81/438 |
| 2006/0065080 A1 * | 3/2006 | Davidson et al. | 81/63 |

FOREIGN PATENT DOCUMENTS

WO    WO 2004/096069    11/2004

* cited by examiner

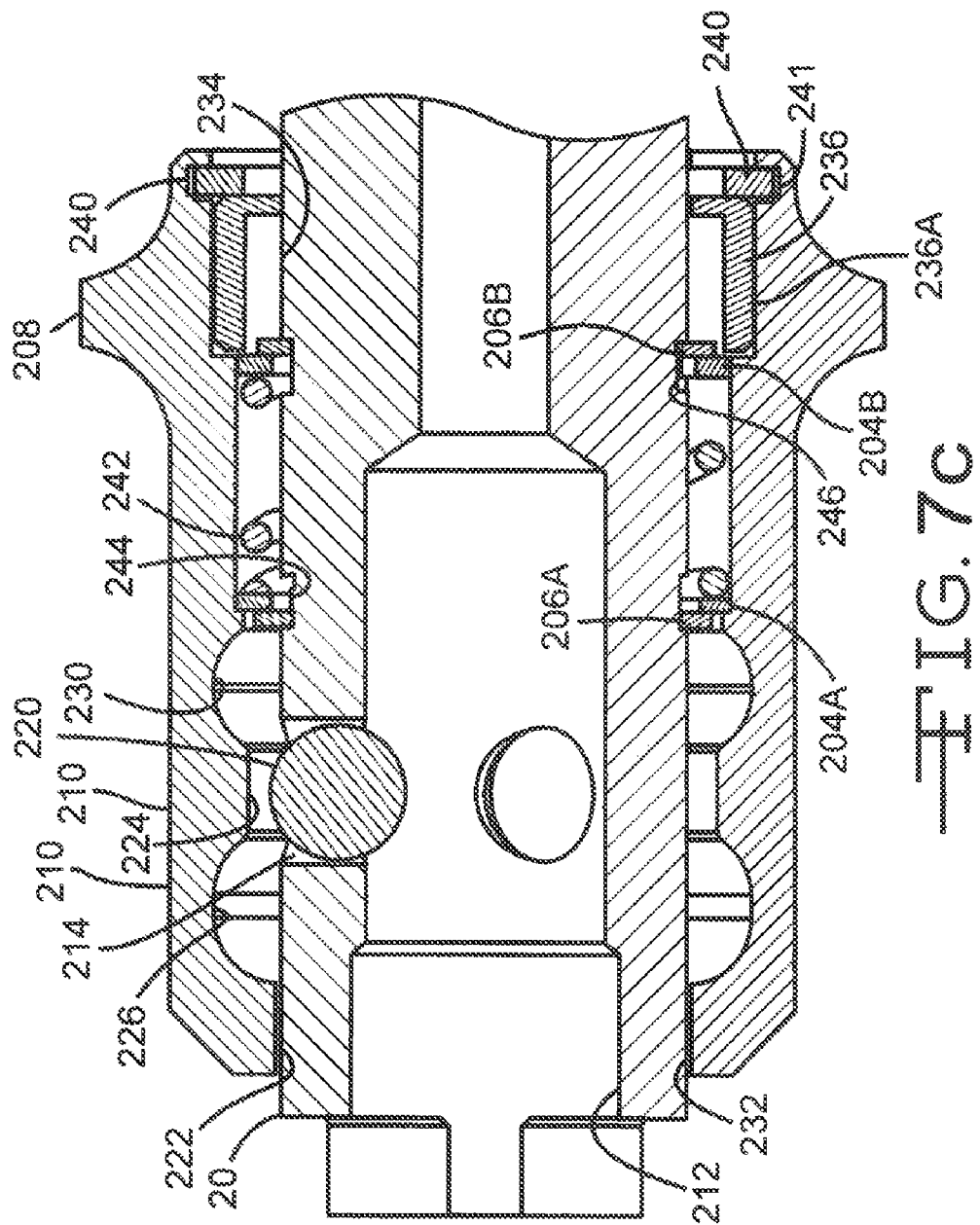

COUPLING DEVICE WITH CONFIGURABLE ACTUATOR

CROSS REFERENCE TO RELATED APPLICATIONS

This application is a continuation-in-part application of U.S. patent application Ser. No. 11/244,301, filed Oct. 5, 2005 now abandoned, entitled-RATCHET HANDLE, which claims priority to U.S. Provisional patent application Ser. No. 60/678,245, filed on May 5, 2005, the contents of which are incorporated herein by reference thereto and relied upon.

BACKGROUND OF THE INVENTION

This invention relates to drivers for rotary surgical cutting tools, and, more particularly, to drivers used in maxillo-facial, neuro, dental and orthopedic surgery, including reamer drivers.

Screwdrivers, ratchet drivers, and other hand-held tools are often utilized to insert, remove and/or adjust fasteners attached to various items. The tool is used to rotate the fasteners into or out of apertures in the items to properly position the fasteners with respect to the items. In ratchet drivers, the rotation is controlled such that there is relatively free rotation in one direction and driven, locked rotation in the opposite direction.

Such tools include a coupling device which retains an insert used to drive the fastener or other item. With regards to ratchet tools, users have differing preferences and adhere to varying conventions as to what constitutes intuitive actuation of a mechanism. Because of this, manufacturers must provide different models which, for example, provide the user with a selection of operation that suits his preferences. For example, focus group studies have shown that some users intuitively associate a pushing action with engaging a tool to an insert. Among these users, a significant portion believes that the same action should also enable disengagement of the insert for insertion of a new insert. At the same time, other users polled associate a pulling action to engagement. Among these users, the same action should also enable disengagement of the insert for insertion of the new insert. The remaining believes that a combination of pushing and pulling should engage and/or disengage the insert. Because the prior art ratcheting mechanisms generally include a large number of parts assembled within the housing in order to complete the ratcheting and actuation mechanisms, a large inventory of the differing parts necessary to provide the user with the engagement/disengagement action they intuitively prefer. The complexity of these mechanisms increase the time and expense necessary for manufacturing tools incorporating these prior art ratcheting mechanisms. One significant expense is the inventory expense, which requires that there be sufficient sets of replacement parts to support each model. Another drawback is that as the number of parts which are similar in appearance (but not function) increases, the risk of misassembly or malassembly increases. Such misassembly could cause a component or assembly to disassemble in a patient's body cavity during surgery.

Therefore, what is needed is a simpler mechanism with fewer parts of simpler form. Still further, what is needed is a coupling device design which is configurable to the needs of the user, while minimizing the number of parts the manufacturer must inventory. Still further, what is needed is a coupling device that may be reconfigured for differing actuation without the need for replacing components with new, custom components. What is needed is a means for minimizing the number of parts a reseller or manufacturer must inventory without sacrificing the range of configurations he is able to assemble.

SUMMARY OF THE INVENTION

A surgical ratchet assembly includes a handle, a drive spindle or shank, a ratcheting mechanism, a locking mechanism and a coupling device. The drive spindle is received within the handle in a rotatable relationship with respect thereto. The ratcheting mechanism is interposed between the handle and the driver. The ratcheting mechanism includes a pawl which can be selectively locked out of engagement with a toothed hub via a reverser. A pair of pawls is preferred. A locking mechanism releasably holds the handle to the ratchet mechanism. Cantilever springs bias the pawl into engagement with the toothed hub. The coupling device couples tool bits to the driver.

In a feature of the invention, the coupling device permits actuation of release or engagement of a tool bit in a configurable manner.

The object of the invention is to provide a ratchet that is easy to operate and does so reliably.

Another object of the invention is to provide a simpler mechanism with fewer parts as no mounting pin is required for the biasing springs.

BRIEF DESCRIPTION OF THE DRAWINGS

FIG. 7c is a close up of the coupling end of configuration C of the invention.

DETAILED DESCRIPTION OF THE PREFERRED EMBODIMENT

This invention has structural similarities to U.S. Pat. No. 6,817,458 to Gauthier, and WO 2004/096069, PCT/IB2004/001244, the contents of both of which are incorporated herein by reference and relied upon.

Figure 1:
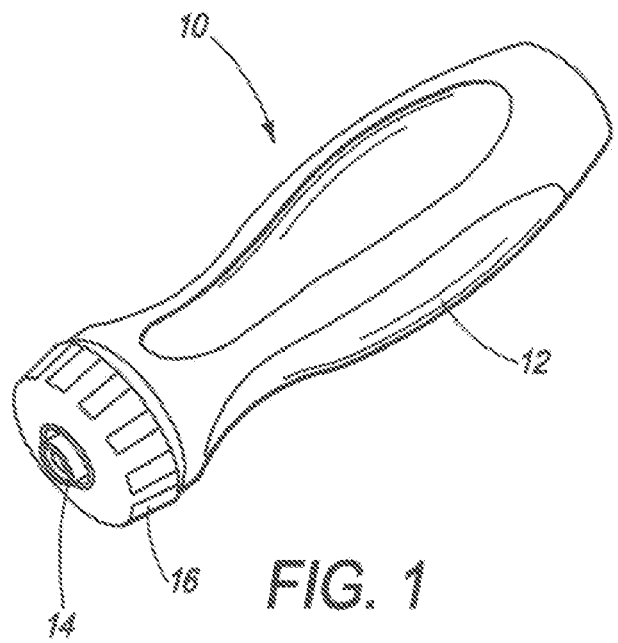
FIG. 1 is a perspective view of the ratchet handle of the invention.

Referring now to FIG. 1, the ratchet handle 10 of the invention is shown, including essentially a handle portion 12, a coupling end 14, and a housing assembly 16 in which is disposed a drive spindle 20 having a toothed hub 22.

Figure 2A:
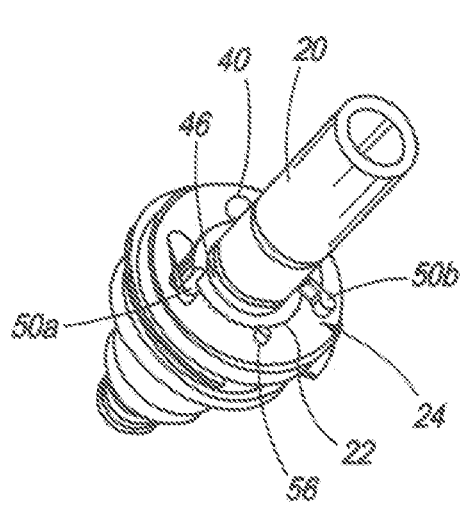
FIG. 2a is a perspective view of the ratchet mechanism of the invention, showing the workings therein.
Figure 2B:
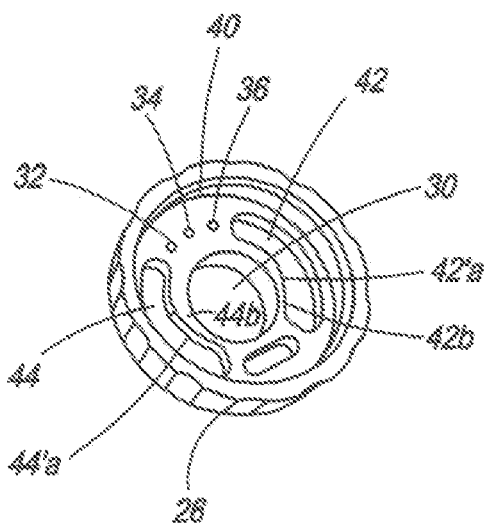
FIG. 2 is a perspective view of the cap reverser of the invention.

Referring now to FIGS. 2a and 2b, a ratchet mechanism 24 is disposed between the toothed hub 22 and the handle 12, in order to enable a user to selectively torque fasteners (not shown), in a desired direction dependent on the position of a reverser 26. The reverser 26 is a cap-shaped structure having an internal aperture 30 and position selection holes 32, 34 and 36 which pass through a wall 38 of the cap. A crest of a ball detent 40 in the housing 48 enters into such holes 32, 34, or 36 to retain the reverser 26 in the desired position (neutral, locked counterclockwise, free rotating clockwise, and vice-versa). Arcuate cutouts 42 and 44 are located on opposite sides of the aperture 30 and are formed to include corresponding cam surfaces 42a and 44a. These cam surfaces 42a and 44a are disposed on an arcuate cam structure 42b and 44b which passes between a centering shoulder 46 and each pawl 50a and 50b such that, the adjacent pawl 50a or 50b may be cammed in or out of engagement with teeth 54 on the toothed hub 22. The pawls 50a and 50b are held in functional relationship by their generally circular stem 50c and 50d, respectively, in arcuate end surfaces 48a and 48b of slots 48c and 48d of a housing 48, into which the pawls are disposed. Elongated, slender wire springs 52a and 52b (which can have a circular cross-section, oval cross-section, an uncut rectangular cross-section, even polygonal cross section, as typically results from a rolled or extruded manufacturing process and not cut, flat sheet processing), preferably made of Nickel-Titanium alloy (a.k.a., "nitinol", from the laboratory that developed it, the Nickel/Titanium/Naval Ordinance Laboratory), a super-elastic, shape memory material, are fixed (using, for example, set screws, or by press fitting, or by a staking operation in the housing, and optionally using a mating nickel-titanium alloy component such as a collet device) in holes 49a and 49b, so as to act as cantilever springs, to urge the pawls 50a and 50b against the teeth 54 of the hub 22. Nitinol alloys have the unusual ability to recover a preset shape, even after drastic distortion. Composition is typically 55%-56% Nickel and 44%-45% Titanium, but slight adjustments of this ratio can significantly impact the properties of the material. There are two primary but overlapping categories of Nitinol. "SuperElastic" alloys are characterized by extraordinary kink resistance and flexibility. The Nitinol Wire used in the invention is a super-elastic alloy which can be strained eight to ten times more than ordinary spring steel without permanent deformation. It can be rather severely compressed, bent or otherwise distorted, but returns to its original shape. This impressive "memory" takes advantage of stress-induced martensitic transformation. In other words, a material is super-elastic when, if sufficient stresses are applied, such materials exhibit martensitic activation/transformation (i.e., deform from an austenitic crystal structure to a stress-induced structure postulated to be martensitic in nature), returning thence to the austenitic state when the stress is removed. The alternate crystal structures described give the alloy super-elastic or pseudo-elastic properties. Poisson's Ratio for nitinol is about 0.3, but this ratio significantly increases up to approximately 0.5 or more when the shape memory alloy is stretched beyond its initial elastic limit. It is at this point that stress-induced martensite is said to occur, i.e., the point beyond which the material is permanently deformed and thus incapable of returning to its initial austenitic shape. Note that although Nickel-Titanium alloys are currently preferred, inexpensive super-elastic steel alloys are now known and of course may be used. The wire used herein has an annealed temper that is straight in shape. A new memory is imparted to the Nitinol wire by restraining the material in exactly the shape required and heating to a temperature above 932° F. (500° C.) for a minimum of five minutes. The shape will be set upon cooling and will exhibit the same flexibility and resistance to deformation as the original wire. And it can be repeatedly retrained to achieve new shapes.

Figure 3:
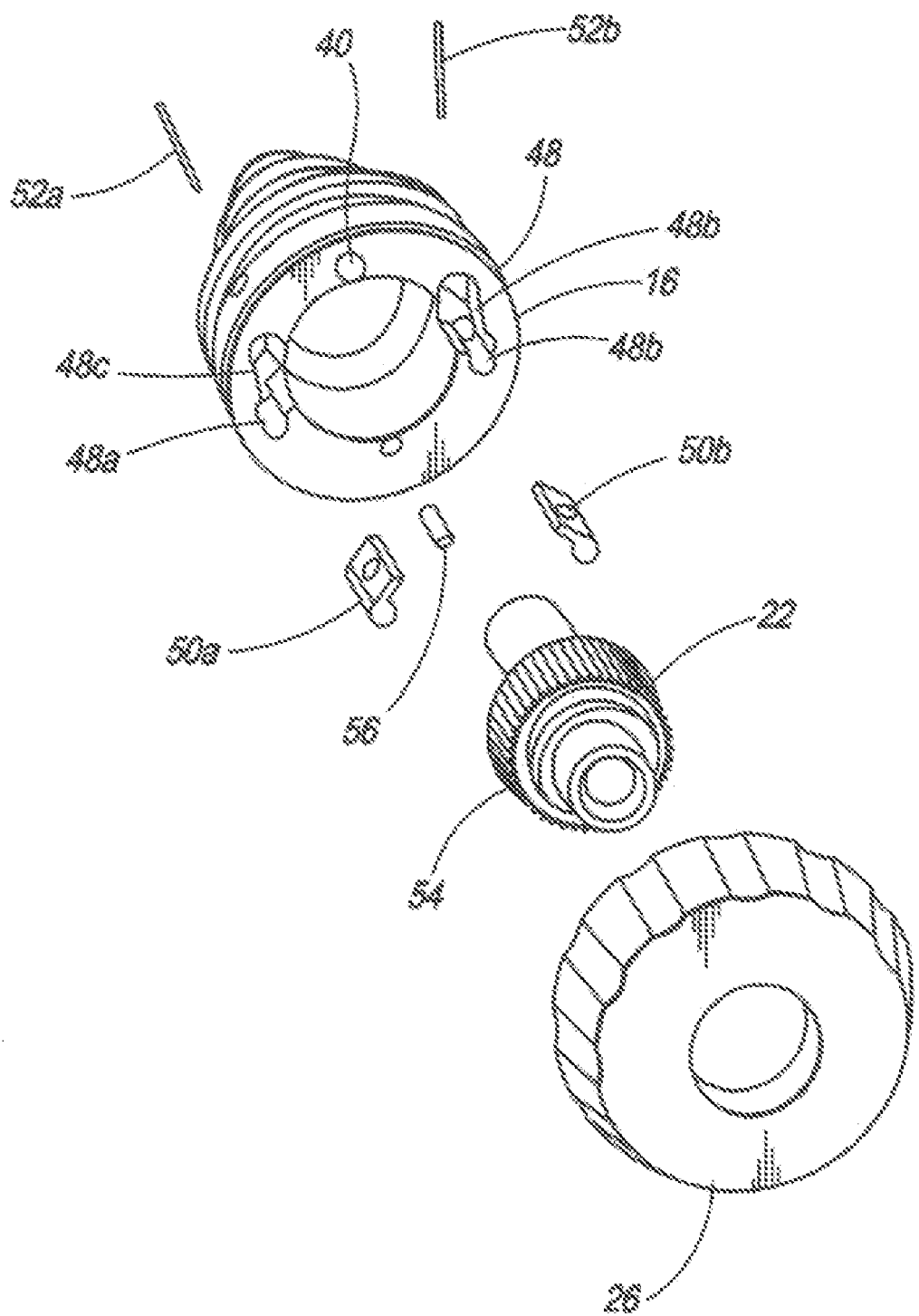
FIG. 3 is an exploded view of the ratchet mechanism 24 of the ratchet handle 10 of the present invention shown in FIG. 1.
Figure 4A:
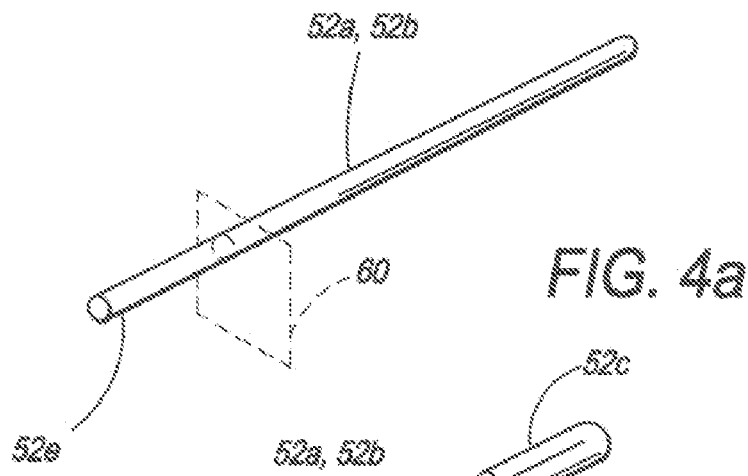
FIG. 4a is a perspective view of an alternate spring of the invention.
Figure 4B:
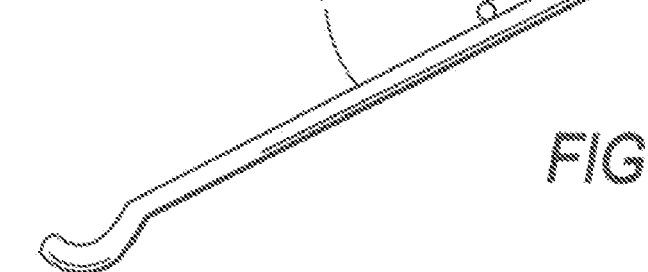
FIG. 4b is a perspective view of another alternate spring of the invention.
Figure 4C:
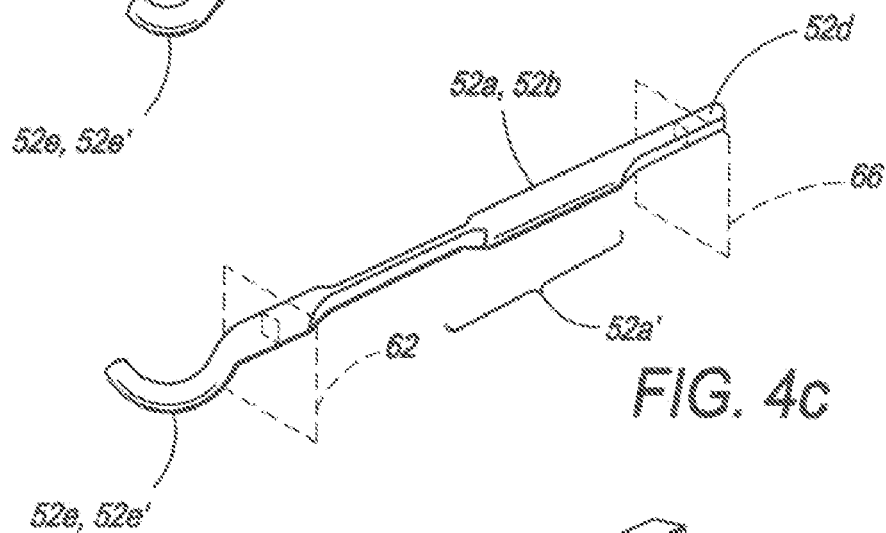
FIG. 4c is a perspective view of still another alternate spring of the invention.
Figure 4D:
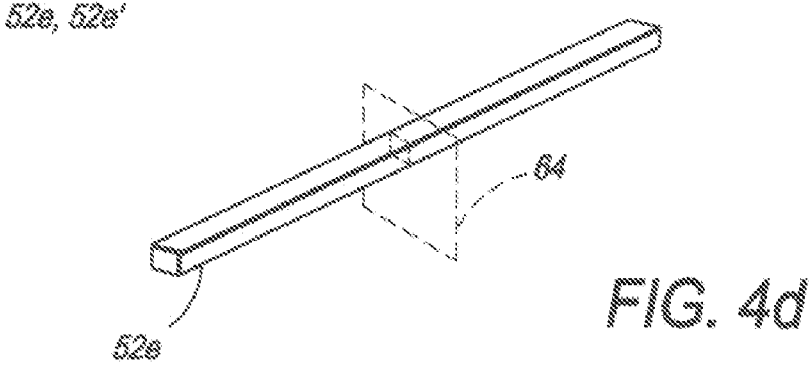
FIG. 4d is a perspective view of still another alternate spring of the invention.

Referring now to FIG. 3, an exploded view of the ratchet mechanism 24 of the invention includes the housing 48, the pawls 50a and 50b, the cantilever springs 52a and 52b, a stop pin 56 (which engages an elongated slot 58 of the reverser 26), the toothed hub 22, and the reverser 26. The stop pin 56 is press fit into the housing 48 so as to fixed therein.

Referring to FIGS. 4a to 4d, suitable wire springs 52a and 52b may have a circular cross-section 60, oval cross-section 62, and uncut rectangular cross-section 64, even polygonal cross section 66, as typically results from a rolled or extruded manufacturing process and not cut flat sheet processing which creates stress risers which limit the functional life of the spring. In addition, the length of the spring 52a, and 52b may be processed so that the cross-section varies in bending moment of inertia along its length 52a', then enabling further control of the biasing forces applied to the pawl 50a and 50b. With spring material such as super-elastic Nitinol or super-elastic steels, controlled processing of the spring 52a or 52b in order to vary and control the bending moment of inertia requires that the spring be formed in an annealed state, prior to heat treating to activate super-elastic properties. Further, where the cross-section is varied in form along the length 52a' of the spring 52a or 52b in a non-symmetrical manner, then, a portion of the end 52c of the spring may be turned up and then against itself, in order to create a feature by which the spring can be held during processing of the non-symmetrical forming of the spring and to enable fixing of the spring in the desired orientation (the orientation that provides the deflection and force characteristics desired). Orientation can be achieved as well via use of a non-round aperture in the housing 48 into which the end 52c is fixed. The spring 52a or 52b may alternatively be deformed at an end 52d to create a feature from which an orientation convention can key off of. Of course, the fixing device (e.g., fastener) must also key off of the non-symmetrical end to orient the spring 52a or 52b properly in the housing 48. In any case, after processing, the cross-section should have overall width dimensions that are substantially the same across the centerline of the wire.

U.S. Pat. No. 5,683,404 to Johnson, entitled "Clamp and Method for its Use", the content of which is incorporated herein by reference thereto, further discusses shape memory materials that are "pseudo-elastic", defining these materials to be super-elastic, because of their ability to exhibit super-elastic/pseudo-elastic recovery characteristics at room temperature.

Thus, a user is able to select which pawl 50a or 50b is engaged, thereby selecting the direction in which the ratchet handle 10 freely rotates which respect to the spindle 20 and the direction in which the pawls 50a or 50b lock the teeth 54 as well as the direction in which the pawls are positioned such that the spindle 20 is free to rotate in the opposite direction. The position of the reverser 26 with respect to the housing assembly 16 is determined by a frictional or interference engagement of a ball-detent 40 in one of the holes 32, 34, or 36.

By adjusting the camming such that in a neutral position, the cam structures 42b and 44b cam both pawls 50a and 50b out of engagement, a free-wheeling mode is possible in which the handle is not locked in either direction. Alternatively, adjusting the camming such that both pawls 50a and 50b are free in a neutral position, ensures that the ratchet mechanism 24 will lock up regardless of the direction in which the handle is torqued with respect to drive spindle 20.

Referring now to FIG. 3, an exploded view of the ratchet mechanism 24 of the invention includes the housing 48, the pawls 50a and 50b, the cantilever springs 52a and 52b, a stop pin 56 (which engages an elongated slot 58 of the reverser 26), the toothed hub 22, and the reverser 26. The stop pin 56 is press fit into the housing 48 so as to be fixed therein.

Figure 5A:
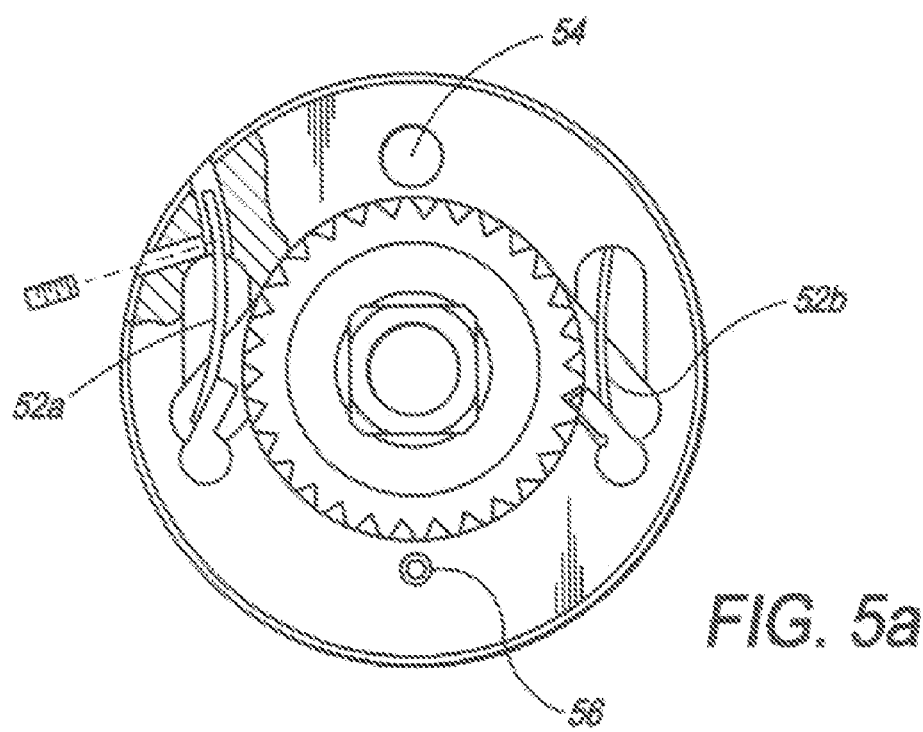
FIG. 5a is a top view showing the positioning of the biasing means against the pawls of the invention.
Figure 5B:
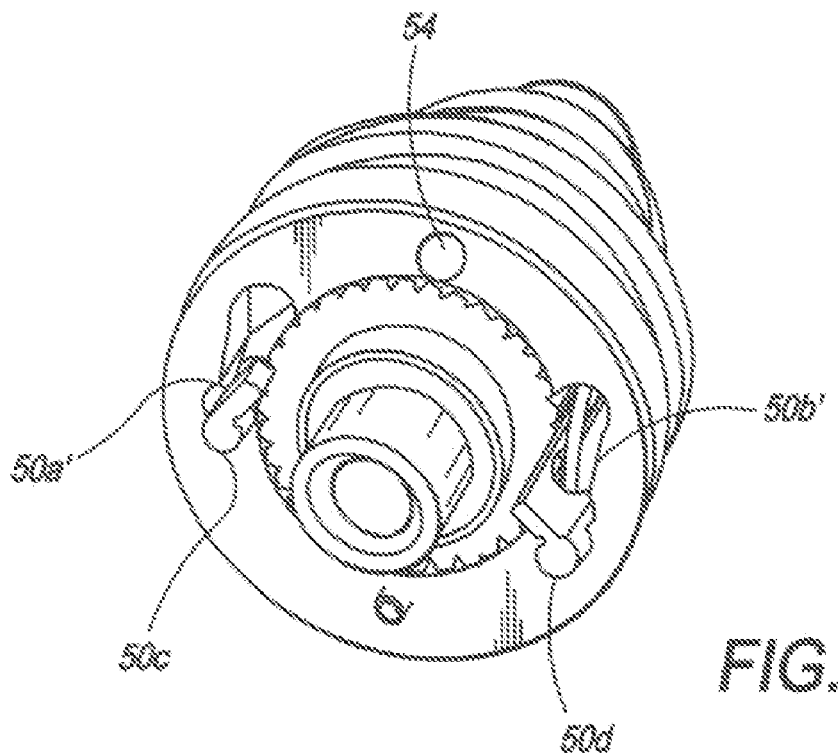
FIG. 5b is a perspective view showing the positioning of the biasing means against the pawls of the invention.

Referring now to FIGS. 5a and 5b the cantilever springs 52a and 52b bias the pawls 50a and 50b against the teeth 54 of the hub 22 wherein the extremities 52e of such springs are disposed in recesses 50a' and 50b' of the pawls. The form of the spring 52a and 52b may be curved in a section 52e', in order to minimize wear on the pawls 50a and 50b.

The springs 52a and 52b are secured to the housing 48 at the first end and free to deflect at the second end. Thus, unlike U.S. Pat. No. 6,817,458 to Gauthier, the biasing members are the cantilevered springs 52a and 52b and not torsional springs. Further, as already mentioned, the cantilever bar of the invention is optionally made of Nitinol, a super-elastic titanium alloy allowing high flexibility and providing a more constant spring force biasing the pawls 50a and 50b against the teeth 54 of the hub 22. A constant biasing force provides smoother ratcheting by avoiding drastic variation in biasing force against the teeth 54, which, if not substantially constant, would cause intermittent dragging of the pawl as it passes from one tooth position to another.

In addition, to further prevent the reverser 26 from rotating past the depressions therein (ref. column 6, line 6, Gauthier '458), the stop pin 56, which is separate from the biasing members 52a and 52b, engages a slot in the cap reverser, similar to Tiede, U.S. Pat. No. 5,613,585 (see column 3, line 25 thereof), the content of which is incorporated herein by reference and relied upon.

Figure 6:
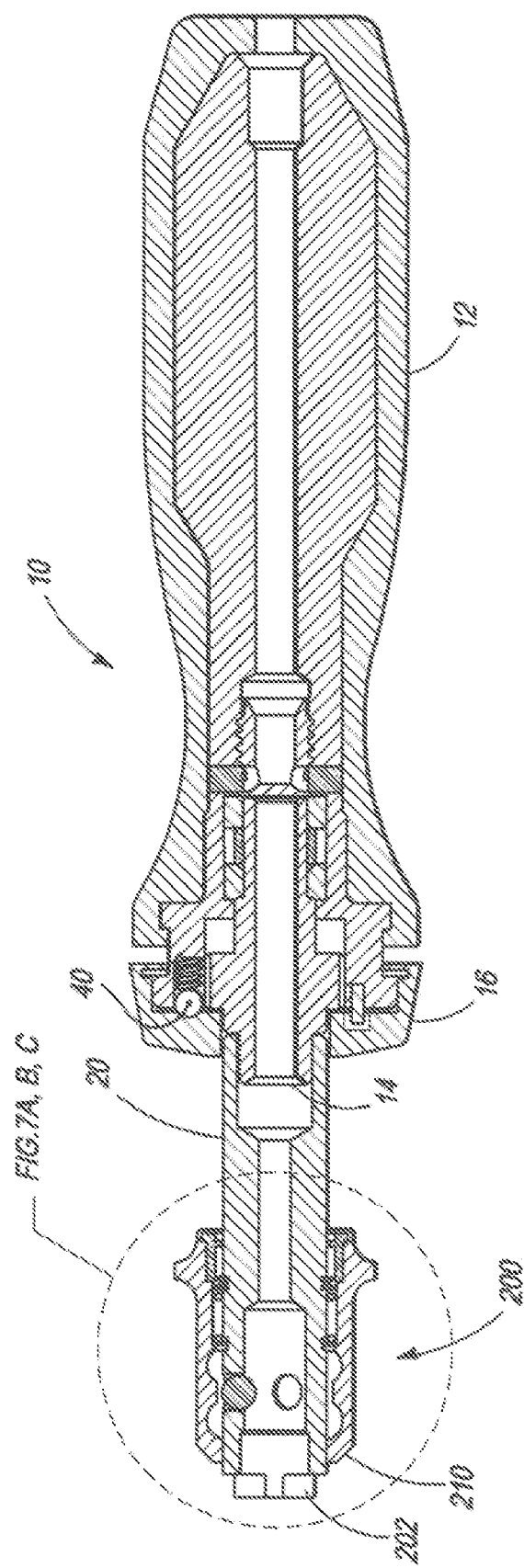
FIG. 6 is a longitudinal cross-section of the invention.

Referring now to FIG. 6, the ratchet handle 10 has a coupling device 200 on a tool bit engaging end 202 of the ratchet handle. Depending on the selection and assembly of washers 204 and retainers 206, the coupling device 200 may be configured in one of three configurations in which the sleeve 210 may be actuated in a selected direction to initiate a particular mechanical response. The first configuration A (shown in FIG. 7a) is a push-to-actuate, push-to-remove configuration. The second configuration B (shown in FIG. 7b) is a pull-to-actuate, pull-to-remove configuration. The third configuration C (shown in FIG. 7c) is a push or pull actuate or remove configuration.

Figure 7A:
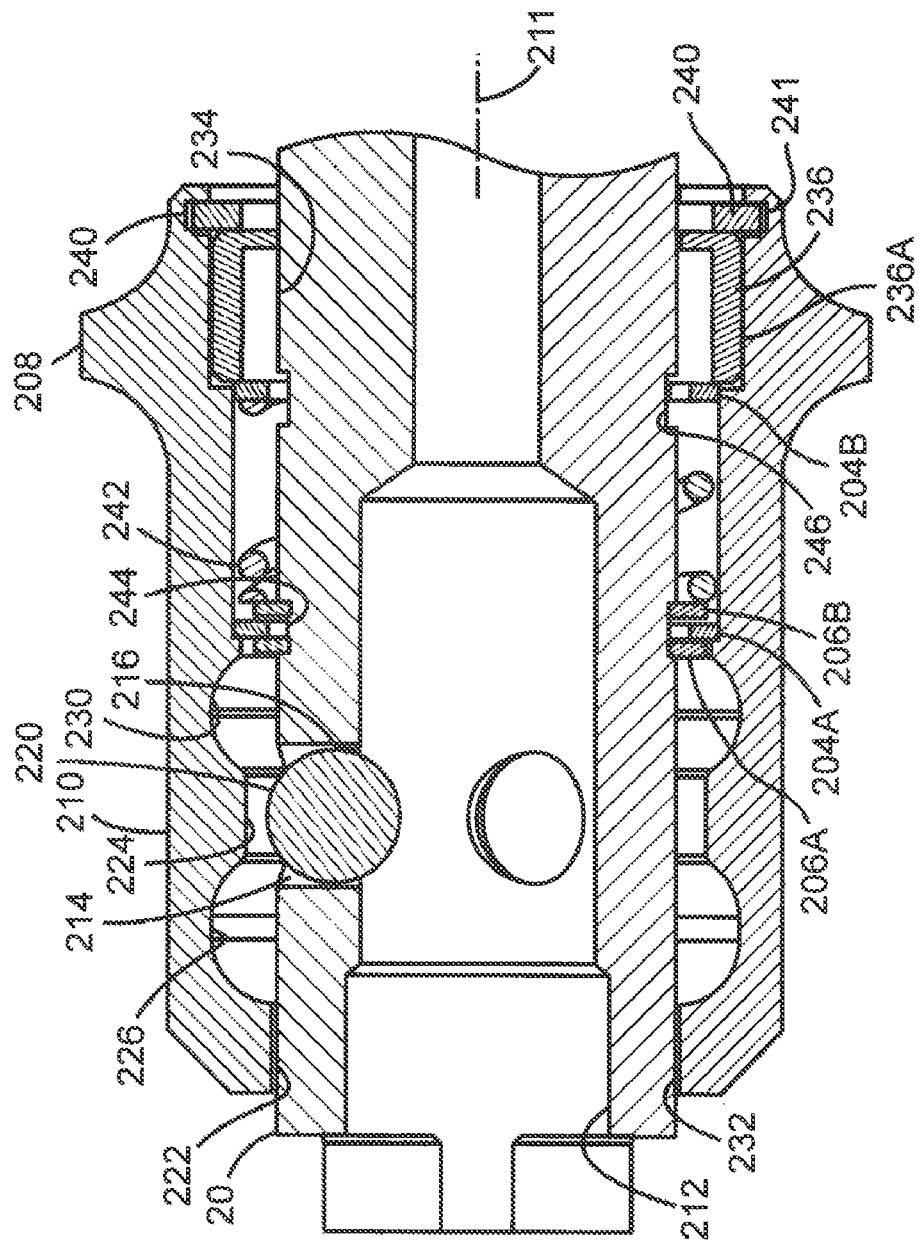
FIG. 7a is a close up of the coupling end of configuration A of the invention.

Referring now to FIG. 7a, the sleeve 210 is a hollow, cylindrical sleeve which is slidably mounted over the drive spindle 20 along an axis 211. The drive spindle 20 includes an interior tool tip engaging interface 212 which is generally cylindrical in form, having one or more transversely milled seats 214 passing substantially through the drive spindle from the outside thereof toward the inside, preferably cut using a ball-end endmill in a manner to leave a small shoulder 216 at the interface between the seat and the interior interface 212, so as to present an obstruction to a ball 220, and consequently, prevent the ball from passing fully into the interior interface, although permitting enough of the ball to penetrate the interior interface 212 to engage into a recess of a tool bit (not shown) when the coupling device 200 is in a locked position, as shown in FIG. 7a. The interior surface 222 of the sleeve 210 includes a ball locking surface 224 interposed between two adjacent ball release recesses 226 and 230. The sleeve 210 is restrained to slide concentric to the axis 211 via a sliding fit between a forward interior cylindrical surface 232 on the tool bit engaging end 202 and via an interior cylindrical surface 234 of a shouldered spacer 236 serving as a proximal sleeve abutment retained in an abutment recess 236A by a first retainer 240 seated in a retainer recess 241. The shoulder spacer 236 holds the first and second spacers 204A, 204B and the second and third retainers 206A, 206B as well as a return spring 242, in an assembled, functional relationship.

Spaced axially toward the rear of the drive spindle 20, a distance approximately the diameter of the ball 220 away from the ball seat 214, a first retainer recess 244 is located. This recess 244 is shallow but wide enough to accommodate the two retainers 206A, 206B and spacer 204A therebetween. An identically formed recess 246 is spaced along the axis still further rearwardly, providing sufficient space therebetween to receive the return spring 242 and to permit sliding movement of the sleeve enough to selectively position either the first ball release recess 226 or the second ball release recess 230 over the ball 220, depending on the particular configuration, thereby enabling selective release of the ball from a locked position. In this figure, a fixed-to-the-drive spindle configuration of second and third retainers 206A, 206B having a first spacer 204A interposed therebetween, is followed by the return spring 242, which is followed by the second spacer 204B which translates with the sleeve 210, thereby permitting a user to react against an annular actuation flange 208 so as to push-to-engage and a push-to-disengage a tool bit in the recess 212.

Figure 7B:
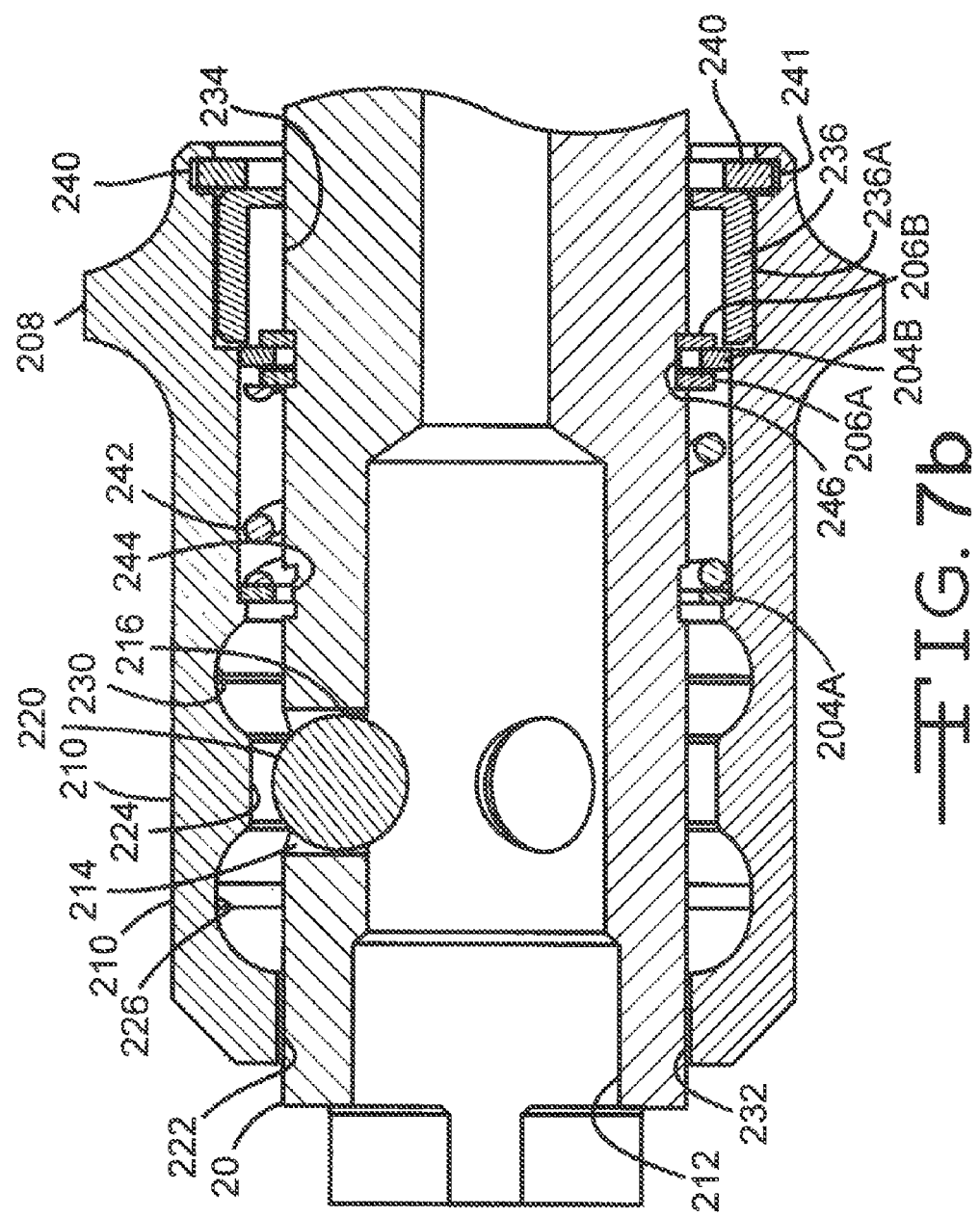
FIG. 7b is a close up of the coupling end of configuration B of the invention.

Referring now to FIG. 7b, configuration B is shown, in which the spacer 204A, which translates with the sleeve 210, is followed by the return spring 242 and then by the second and third retainers 206A, 206B with the second spacer 204B interposed therebetween and fixed to the drive spindle 20 in the second recess 246. This configuration B permits a pull-to-engage, pull-to-disengage configuration.

Referring now to FIG. 7c, configuration C is shown, in which the second retainer 206A, fixed in the first recess 244, is followed by the first spacer 204A, which acts against the return, spring 242 and translates with the sleeve 210, which is then followed the second spacer 204B, and then the third retainer 206B, which is fixed in the second recess 246.

Figure 8:
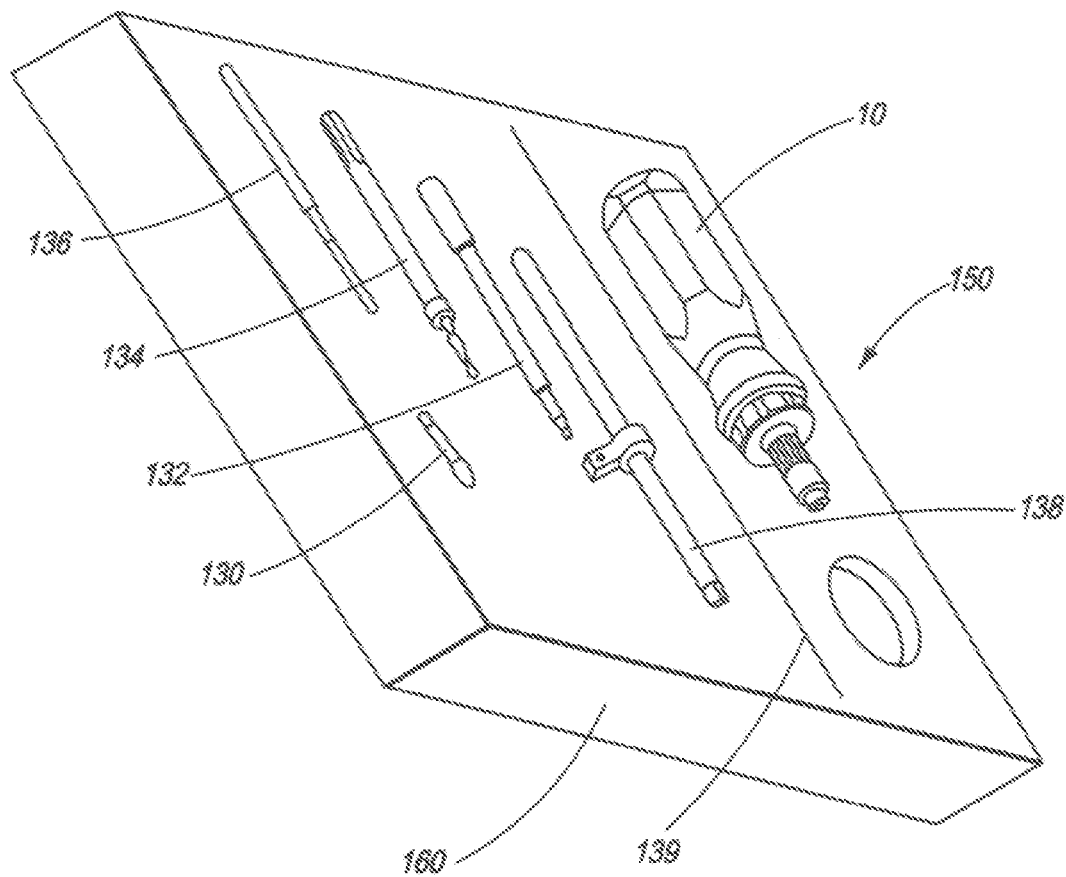
FIG. 8 is a perspective view of a kit of the invention.

Referring now to FIG. 8, the kit 150 is shown, including the ratchet 10, tools 130, 132, 134, 136, a T-bar 138 and a guide pin 139. The components of the kit 150 are organized in a case 160 having recesses into which the ratchet and the tools may be conveniently stored until use. A selection of surgical fasteners and, optionally, bone plates and other hardware, as well as ancillary tools may be conveniently stored until needed in a particular surgical protocol.

In an advantage of the invention, a simpler mechanism with fewer parts of simpler form is provided.

In another advantage, a coupling device design is provided which is configurable to the needs of the user, while minimizing the number of parts the manufacturer must inventory.

In another advantage, a coupling device is provided which may be reconfigured for differing actuation without the need for replacing components with new, custom or use-specific components.

In another advantage, a ratchet handle is provided which minimizes the number of parts a reseller or manufacturer must inventory without sacrificing the range of configurations he is able to assemble.

In another advantage of the invention, the cantilever form of the springs 52a and 52b, together with the fact that the springs are made of super-elastic material provide a lasting, reliable activation of the pawls 50a and 50b and long life to the ratchet.

In another advantage, the cantilever form of the springs 52a and 52b and the use of nickel-titanium in the construction of the cantilever springs enables the springs to exert a nearly constant biasing force biasing the pawls so as to engage them with the hub 22.

In another advantage, the narrow form of the springs 52a and 52b permit the bulk of the ratchet mechanism to be reduced without sacrificing strength or reliability.

In another advantage, the cantilever springs 52a and 52b enter the housing 48 from the side of the housing, thus permitting maintenance and/or replacement of such springs without having to disassemble the housing assembly 16 (e.g., removing the reverser is not necessary to access the springs).

In another advantage, the reverser 26 includes a position in which both pawls 50a and 50b are in an engaged position, thus locking the ratchet mechanism against free movement in either direction.

The object of the invention is to provide a ratchet 10 that is easy to operate and does so reliably.

Another object of the invention is to provide a range of ratchet handles with a simpler mechanism with fewer parts to inventory while not sacrificing the resellers ability to configure the actuation of the handle to the preferences of the customer.

Another object of the invention is to provide a ratchet in which no mounting pin is required for the biasing springs 52a or 52b.

Although the term "driver" may be used herein, this term is meant to encompass taps, guide pins, screwdrivers, reamer drivers and any tool which needs to be fastened and held, even rotated, in a controlled manner.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A tool bit coupling for selectively retaining and releasing a tool bit, the coupling comprising:
   a) a shank comprising at least one ball recess extending through a thickness of the shank from an exterior surface to an interior interface adapted for receiving a tool bit, wherein the shank further comprises a first retainer recess spaced apart along the exterior surface from a second retainer recess;
   b) a ball received in the ball recess substantially extending into the shank interior interface so as to permit the ball to enter into engagement with a tool bit to retain the tool bit with the coupling;
   c) a sleeve mounted in an axially manipulatable relationship on the shank, the sleeve comprising a first interior ball release recess followed by an interior ball locking surface and then a second interior ball release recess, wherein the first and second ball release recesses and the intermediate ball locking surface are selectively displaceable over the ball recess of the shank; and
   d) a spring disposed between the shank and the sleeve and comprising first and second spring ends biasing respective first and second spacers disposed between the shank and the sleeve, wherein the spring biases the first spacer into contact with a distal sleeve abutment spaced from the second ball release recess and biases the second spacer into contact with a proximal sleeve abutment spaced from the second ball release recess and the first sleeve abutment;
   e) wherein the proximal sleeve abutment is removably disposed between the shank and the sleeve in an abutment recess and comprises spaced apart first and second proximal sleeve abutment ends and wherein the first proximal sleeve abutment end is adjacent to the second retainer recess and the second proximal sleeve abutment end is biased against a first retainer removably disposed between the shank and the sleeve in a sleeve retainer recess;
   f) wherein with the ball received in the ball recess of the shank and being radially aligned with the ball locking surface of the sleeve, the first and second retainer recesses of the shank are axially offset from the first and second ball release recesses and the intermediate ball locking surface of the sleeve;
   g) wherein with the first retainer and the proximal sleeve abutment removed from between the shank and the sleeve, the coupling is manipulatable into the following configurations so that manipulation of the sleeve effects selective retainment and release of a tool bit from the coupling, including:
      i) in a first coupling configuration, wherein the first spacer intermediate second and third retainers seated in the first retainer recess contacts the distal sleeve abutment by the spring biasing between the third retainer and the second spacer contacting the proximal sleeve abutment so that the sleeve and second spacer are only axially manipulatable in a distal direction against the bias of the spring moved into a state of compression to thereby remove the first spacer from contact with the distal sleeve abutment to position the second interior ball release recess over the ball so that the ball is movable out of the ball recess in the shank to selectively release a tool bit from the coupling and then the sleeve is axially manipulatable in a proximal direction to retain a tool bit in the coupling as the spring uncompresses to move the interior ball locking surface into a position disposed over the ball recess as the first spacer re-contacts the distal sleeve abutment;
      ii) in a second coupling configuration, wherein the second spacer intermediate the second and third retainers seated in the second recess contacts the proximal sleeve abutment by the spring biasing between the second retainer and the first spacer contacting the distal sleeve abutment so that the sleeve and the first spacer are only axially manipulatable in a proximal direction against the bias of the spring moved into a state of compression to thereby remove the second spacer from contact with the proximal sleeve abutment to position the first interior ball release recess over the ball so that the ball is movable out of the ball recess in the shank to selectively release a tool bit from the coupling and then the sleeve is axially manipulatable in a distal direction to retain a tool bit in the coupling as the spring uncompresses to move the interior ball locking surface into a position disposed over the ball recess as the second spacer re-contacts the proximal sleeve abutment; and
      iii) in a third coupling configuration, the second and third retainers are seated in the respective first and second retainer recesses with the first and second spacers biased against the respective second and third retainers and into contact with the respective distal and proximal sleeve abutments by the spring so that the sleeve is axially manipulatable in either a distal or a proximal direction against the bias of the spring moved into a state of compression to thereby remove either the first or the second spacer from contact with the respective distal or proximal sleeve abutment to position the respective first or second interior ball release recess over the ball so that the ball is movable out of the ball recess in the shank to selectively release a tool bit from the coupling and then the sleeve is axially manipulatable in a reverse direction to retain a tool bit in the coupling as the spring uncompresses to move the interior ball locking surface into a position disposed over the ball recess as the first or the second spacer re-contacts the respective distal or proximal sleeve abutment.

2. The tool bit coupling of claim 1, wherein the spring is made of a super-elastic material.

3. The tool bit coupling of claim 1 as part of a ratchet tool having a ratchet mechanism comprising:
 a) a housing;
 b) a toothed hub supported by the housing;
 c) at least one pawl pivotally disposed in the housing; and
 d) at least one cantilever spring biasing the at least one pawl into engagement with corresponding ratchet teeth of the toothed hub.

4. The tool bit coupling of claim 3, wherein the cantilever spring is fixed via a fastening device in the side of the housing.

5. The tool bit coupling of claim 3, wherein the cantilever spring is fixed via a staking operation in the side of the housing.

6. The tool bit coupling of claim 3, wherein the cantilever spring is slender and substantially straight.

7. The tool bit coupling of claim 3, wherein the cantilever spring is made of a super-elastic material.

8. The tool bit coupling of claim 3, further including a reverser disposed in a structure to rotate with respect to the housing.

9. The tool bit coupling of claim 8 wherein the reverser is adapted to selectively move the at least one pawl into and out of engagement with ratchet teeth on the toothed hub to select between positive torque throughput of the coupling device when rotated in one direction and free rotation when rotated in another direction.

10. The tool bit coupling of claim 8, wherein the reverser is adapted to selectively move the at least one pawl into and out of engagement with the ratchet teeth to enable selection between positive torque throughput of the coupling device and free-wheeling.

11. The tool bit coupling of claim 8 wherein the ratcheting tool includes at least two opposed pawls against which the reverser acts to selectively move one pawl out of engagement with the ratchet teeth while the other is permitted to engage the ratchet teeth, thereby enabling reversing of the direction of ratcheting and positive throughput.

12. The tool bit coupling of claim 8 wherein the housing comprises at least one slot and the reverser includes at least one recess aligned with and disposed at least partially above the at least one slot in the housing so that rotational movement of the reverser causes selective engagement of the recess with the at least one pawl to thereby selectively move the pawl into and out of engagement with teeth on a toothed hub to select between positive torque throughput of the coupling device and free-rotation.

13. The tool hit coupling of claim 12 wherein a stop pin fixed to the housing engages a slot in the reverser to limit rotational movement of the reverser between two positions.

14. The tool bit coupling of claim 3 wherein the housing comprises at least one slot including a generally arcuate end circumscribing an angle of greater than 180 degrees.

15. The tool bit coupling of claim 14, wherein at least one pawl is disposed in the at least one slot, the pawl including a generally circular stem at one end that is rotatably engaged within the arcuate end of the slot.

16. The tool bit coupling of claim 3 wherein the cantilever spring enters through an aperture in a side of the housing.

17. The tool bit coupling of claim 1 wherein each of the first and second retainer recesses has a width that is sufficient to seat a first retainer and a second retainer sandwiching a spacer therebetween.

18. The tool bit coupling of claim 1 wherein the spring is a coil spring.

19. The tool bit coupling of claim 1 wherein the first and second spacers and the first and second retainers are annular members.

20. A ratcheting tool comprising the tool bit coupling of claim 1 and further including a ratcheting mechanism comprising:
 a) a housing attached to the shank and comprising a pair of slots, each slot, including a generally arcuate end circumscribing an angle of greater than 180 degrees;
 b) a pair of pawls, one of the pawls being pivotally disposed in one of the slots in the housing;
 c) a cantilever spring engaged with each of the pawls to selectively bias them into engagement with corresponding ratchet teeth of a toothed hub supported by the housing, wherein each pawl comprises a generally circular stem at one end that is rotatably engaged within the arcuate end of the slot; and
 d) a reverser disposed in a structure to rotate with respect to the housing, the reverser comprising at least one recess aligned with and disposed at least partially above the at least one slot in the housing, wherein rotational movement of the reverser effects selective movement of one of the pawls into and out of engagement with teeth on a toothed hub to thereby select between positive torque throughput of the coupling device and free-rotation.

21. A kit for surgical use, the kit including
 a) the ratcheting tool of claim 20; and
 b) a selection of surgical fasteners and a case having recesses into which the ratchet and the tools may be conveniently stored until use.

22. The ratchet tool of claim 20 wherein a stop pin fixed to the housing engages a slot in the reverser to limit rotational movement of the reverser between two positions.

23. A tool bit coupling for selectively retaining and releasing a tool bit, the coupling comprising:
 a) a shank comprising at least one ball recess extending through a thickness of the shank from an exterior surface to an interior interface adapted for receiving a tool bit, wherein the shank further comprises a first annular retainer recess spaced apart along the exterior surface from a second annular retainer recess and wherein each of the first and second annular retainer recesses has a width that is sufficient to seat a first annular retainer and a second annular retainer sandwiching an annular spacer therebetween;
 b) a ball received in the ball recess substantially extending into the shank interior interface so as to permit the ball to enter into engagement with a tool bit to retain the tool bit with the coupling;
 c) a sleeve mounted in an axially manipulatable relationship on the shank, the sleeve comprising a first interior annular ball release recess followed by an interior annular ball locking surface and then a second interior annular ball release recess, wherein the first and second ball release recesses and the intermediate ball locking surface are selectively displaceable over the ball recess of the shank; and d) a coil spring disposed between the shank and the sleeve and comprising first and second spring ends biasing respective first and second annular spacers disposed between the shank and the sleeve, wherein the coil spring biases the first annular spacer into contact with a distal sleeve abutment spaced from the second ball release recess and biases the second annular spacer into contact with a proximal sleeve abutment spaced from the second ball release recess and the first sleeve abutment;

e) wherein the proximal sleeve abutment is removably disposed between the shank and the sleeve in an abutment recess and comprises spaced apart first and second proximal sleeve abutment ends and wherein the first proximal sleeve abutment end is adjacent to the second retainer recess and the second proximal sleeve abutment end is biased against a first retainer removably disposed between the shank and the sleeve;

f) wherein with the ball received in the ball recess of the shank and being radially aligned with the ball locking surface of the sleeve, the first and second retainer recesses of the shank are axially offset from the first and second ball release recesses and the intermediate ball locking surface of the sleeve;

g) wherein the first retainer and the proximal sleeve abutment are manipulatable so that a spacer is positionable intermediate the first and second retainers seated in either the first or the second retainer recess to thereby contact the distal or the proximal sleeve abutment by the coil spring biasing between one of the retainers and the other spacer contacting the other of the distal and proximal sleeve abutment, so that the sleeve is only axially manipulatable in a direction toward the spacer disposed intermediate the second and third retainers and against the bias of the coil spring moved into a state of compression to thereby remove the first or the second spacer from contact with the respective distal or proximal sleeve abutment to position one or the other of the interior ball release recesses over the ball so that the ball is movable out of the ball recess in the shank to selectively release a tool bit from the coupling and then the sleeve is axially manipulatable in a reverse direction to retain a tool bit in the coupling as the coil spring uncompresses to move the interior ball locking surface into a position disposed over the ball recess as the first or the second spacer re-contacts the respective distal or proximal sleeve abutment; and h) wherein the first retainer and the proximal sleeve abutment are manipulatable so that the second and third retainers are positionable to seat in the respective first and second retainer recesses with the first and second spacers biased against the respective second and third retainers and into contact with the respective distal and proximal sleeve abutments by the coil spring, so that the sleeve is axially manipulatable in either a distal or a proximal direction against the bias of the coil spring moved into a state of compression to thereby remove either the first or the second spacer from contact with the respective distal or proximal sleeve abutment to position the respective first or second interior ball release recess over the ball so that the ball is movable out of the ball recess in the shank to selectively release a tool bit from the coupling and then the sleeve is axially manipulatable in a reverse direction to retain a tool bit in the coupling as the coil spring uncompresses to move the interior ball locking surface into a position disposed over the ball recess as the first or the second spacer re-contacts the respective distal or proximal sleeve abutment.

24. A tool bit coupling for selectively retaining and releasing a tool bit, the coupling comprising:

a) a shank comprising at least one ball recess extending through a thickness of the shank from an exterior surface to an interior interface adapted for receiving a tool bit, wherein the shank further comprises a first retainer recess spaced apart along the exterior surface from a second retainer recess;

b) a ball received in the ball recess substantially extending into the shank interior interface so as to permit the ball to enter into engagement with a tool bit to retain the tool bit with the coupling;

c) a sleeve mounted in an axially manipulatable relationship on the shank, the sleeve comprising a first interior ball release recess followed by an interior ball locking surface and then a second interior ball release recess, wherein the first and second ball release recesses and the intermediate ball locking surface are selectively displaceable over the ball recess of the shank; and d) a spring disposed between the shank and the sleeve and comprising first and second spring ends biasing respective first and second spacers disposed between the shank and the sleeve, wherein the spring biases the first spacer into contact with a distal sleeve abutment spaced from the second ball release recess and biases the second spacer into contact with a proximal sleeve abutment spaced from the second ball release recess and the first sleeve abutment;

e) wherein the proximal sleeve abutment is removably disposed between the shank and the sleeve in an abutment recess and comprises spaced apart first and second proximal sleeve abutment ends and wherein the first proximal sleeve abutment end is adjacent to the second retainer recess and the second proximal sleeve abutment end is biased against a first retainer removably disposed between the shank and the sleeve;

f) wherein with the ball received in the ball recess of the shank and being radially aligned with the ball locking surface of the sleeve, the first and second retainer recesses of the shank are axially offset in a proximal direction from the first and second ball release recesses and the intermediate ball locking surface of the sleeve;

g) wherein the first retainer and the proximal sleeve abutment are manipulatable so that a spacer is positionable intermediate the first and second retainers seated in either the first or the second retainer recess to thereby contact the distal or the proximal sleeve abutment by the spring biasing between one of the retainers and the other spacer contacting the other of the distal and proximal sleeve abutment, so that the sleeve is only axially manipulatable in a direction toward the spacer disposed intermediate the second and third retainers and against the bias of the spring moved into a state of compression to thereby remove the first or the second spacer from contact with the respective distal or proximal sleeve abutment to position one or the other of the interior ball release recesses over the ball so that the ball is movable out of the ball recess in the shank to selectively release a tool bit from the coupling and then the sleeve is axially manipulatable in a reverse direction to retain a tool bit in the coupling as the spring uncompresses to move the interior ball locking surface into a position disposed over the ball recess as the first or the second spacer re-contacts the respective distal or proximal sleeve abutment; and h) wherein the first retainer and the proximal sleeve abutment are manipulatable so that the second and third retainers are positionable to seat in the respective first and second retainer recesses with the first and second spacers biased against the respective second and third retainers and into contact with the respective distal and proximal sleeve abutments by the spring, so that the sleeve is axially manipulatable in either a distal or a proximal direction against the bias of the spring moved into a state of compression to thereby remove either the first or second spacer from contact with the respective distal or proximal sleeve abutment to position the respective first or second interior ball release recess over the ball so that the ball is movable out of the ball recess in the shank to selectively release a tool bit from the coupling and then the sleeve is axially manipulatable in a reverse direction to retain a tool bit in the coupling as the spring uncompresses to move the interior ball locking surface into a position disposed over the ball recess as the first or the second spacer re-contacts the respective distal or proximal sleeve abutment.

\* \* \* \* \*